United States Patent
Ramsteiner et al.

(10) Patent No.: US 10,466,203 B2
(45) Date of Patent: Nov. 5, 2019

(54) ACOUSTIC MONITORING DEVICE FOR FUEL QUALITY

(71) Applicant: Robert Bosch GmbH, Stuttgart (DE)

(72) Inventors: Ingo Ramsteiner, Stuttgart (DE); Karl Bendel, Schwieberdingen (DE); Volker Leifert, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 145 days.

(21) Appl. No.: 15/532,581

(22) PCT Filed: Oct. 27, 2015

(86) PCT No.: PCT/EP2015/074907
§ 371 (c)(1),
(2) Date: Jun. 2, 2017

(87) PCT Pub. No.: WO2016/087129
PCT Pub. Date: Jun. 9, 2016

(65) Prior Publication Data
US 2017/0343513 A1 Nov. 30, 2017

(30) Foreign Application Priority Data
Dec. 3, 2014 (DE) ........................ 10 2014 224 719

(51) Int. Cl.
*G01N 29/032* (2006.01)
*G01N 29/14* (2006.01)
(Continued)

(52) U.S. Cl.
CPC ....... *G01N 29/032* (2013.01); *F02D 19/0634* (2013.01); *G01N 29/221* (2013.01);
(Continued)

(58) Field of Classification Search
CPC ...... G01N 25/08; G01N 25/085; G01N 29/02; G01N 29/14; G01N 29/222
See application file for complete search history.

(56) References Cited

U.S. PATENT DOCUMENTS 3,264,863 A * 8/1966 Maropis ................. G01K 11/22
374/27
3,608,715 A * 9/1971 Snyder ................... G01N 29/02
209/590

(Continued)

FOREIGN PATENT DOCUMENTS

DE 3146638 7/1983
GB 1350973 A * 4/1974
(Continued)

OTHER PUBLICATIONS

International Search Report for Application No. PCT/EP2015/074907 dated Feb. 26, 2016 (English Translation, 2 pages).

*Primary Examiner* — David A Rogers
(74) *Attorney, Agent, or Firm* — Michael Best & Friedrich LLP

(57) ABSTRACT

Within the scope of the invention, a device for monitoring the quality of a fuel stored in a fuel tank has been developed. The main field of application is diesel-operated vehicles. The fuel is therefore preferably diesel fuel. The device is defined by the fact that means for determining the boiling point of the fuel are provided. Furthermore, a method for monitoring the quality of a fuel stored in a fuel tank has also been developed within the scope of the invention. The main field of application is diesel-operated vehicles. The fuel is therefore preferably diesel fuel. The method is defined by the fact that the boiling point of the fuel or a deviation of this boiling point from a normal value is measured. During the analysis of real injection pumps which have failed it has been detected that an excessively low boiling point of the (Continued)

fuel can cause the fuel to outgas. As a result, bubbles in which the necessary lubrication is no longer provided locally form in the injection pump. Furthermore, the lubricating effect is dependent on the fuel having a certain minimum viscosity. A low boiling point is also correlated with a low viscosity. Therefore, overall, the boiling point (initial boiling point, IBP) is a particularly good indicator especially of those deviations from standard values for the fuel which entail particularly costly damage.

20 Claims, 1 Drawing Sheet

(51) Int. Cl.
G01N 29/22 (2006.01)
G01N 29/44 (2006.01)
G01N 33/22 (2006.01)
F02D 19/06 (2006.01)
F02D 41/00 (2006.01)
F02B 3/06 (2006.01)

(52) U.S. Cl.
CPC ...... *G01N 33/22* (2013.01); *F02D 2200/0611* (2013.01); *G01N 2291/022* (2013.01); *G01N 2291/02433* (2013.01); *G01N 2291/02881* (2013.01)

(56) References Cited

U.S. PATENT DOCUMENTS

| 2002/0197182 A1* | 12/2002 | Minter | A61L 2/025 422/20 |
| 2003/0230249 A1 | 12/2003 | Yamaoka et al. | |
| 2010/0193349 A1* | 8/2010 | Braam | B06B 3/00 204/157.15 |
| 2013/0269243 A1* | 10/2013 | Lund | F02B 13/00 44/458 |

FOREIGN PATENT DOCUMENTS

| GB | 2275107 | 8/1994 |
| WO | 1999048846 | 9/1999 |
| WO | 2007084406 | 7/2007 |

* cited by examiner

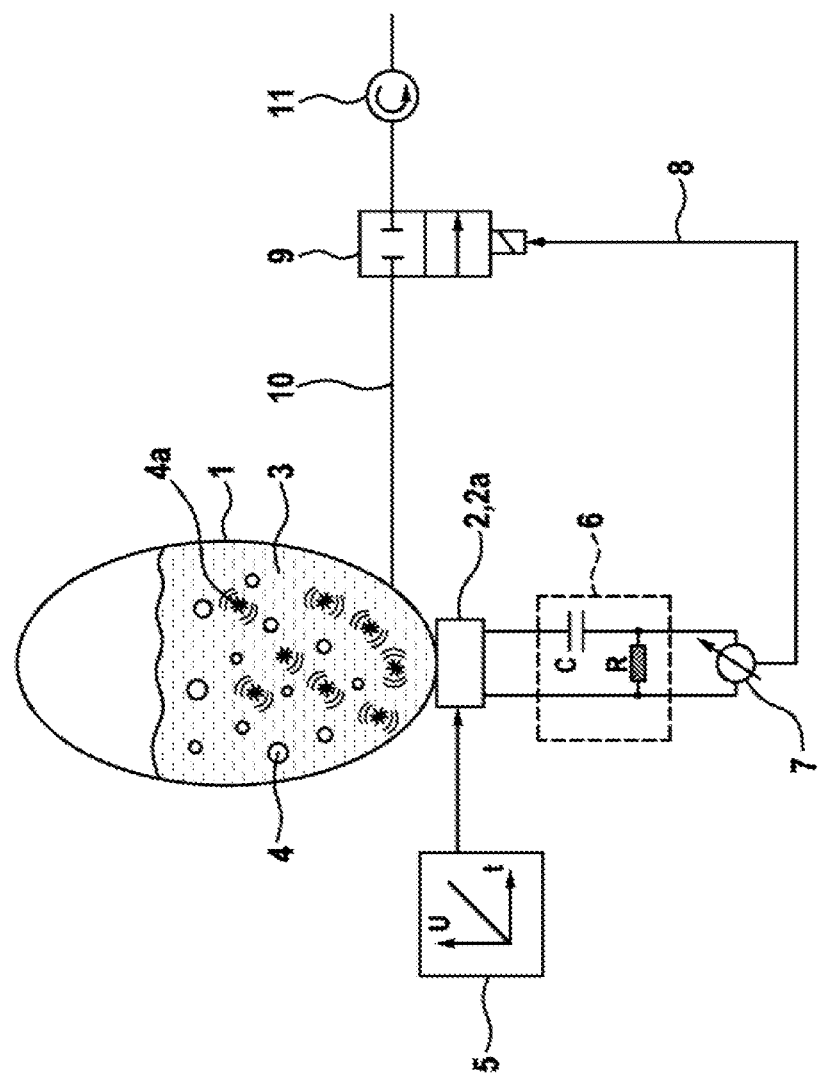

ACOUSTIC MONITORING DEVICE FOR FUEL QUALITY

BACKGROUND OF THE INVENTION

The present invention concerns a device and a method for monitoring the quality of a fuel stored in a fuel tank.

In modern diesel vehicles, the injection system, and here in particular the high-pressure injection pump, must be lubricated by the diesel fuel. If said systems run dry only locally, as a rule an immediate failure is the result. Repair costs of several thousand euros must then be reckoned with.

Such failures occur if diesel is contaminated with gasoline by incorrect refueling, for example. Because the fuel dispensing pistols for gasoline have a smaller diameter than the fuel dispensing pistols for diesel, such an operating error at the fuel station cannot be prevented. Damage to the injection system, however, does not requires said worst operating mistake. The more power a diesel engine draws from the same engine displacement, the more the injection system requires the fueled diesel to correspond exactly to the specification. The corresponding tolerances are narrower with every new generation of engines. Already a small contamination of the diesel fuel with water or other substances can lead to greatly increased wear or even to an immediate failure of the injection system.

Said problem is occurring more frequently since high end injection systems are also being operated in countries in which the development of the infrastructure for the fuel supply has not kept in step with the development of the injection systems.

Methods are known from WO 2007 084 406 A2 and from WO 1999 048 846 A1 with which the quality of a fuel can be measured by means of infrared spectroscopy. It is a disadvantage that said methods require a complicated and bulky optical design, so that they are not practical for use in vehicles.

SUMMARY OF THE INVENTION

It is therefore the object of the invention to provide means in the vehicle for monitoring the fuel quality, with which the described failures and corresponding expensive large repairs can be avoided.

This object is achieved according to the invention by a device and by a method. Further advantageous embodiments result from the claims.

Within the scope of the invention, a device for monitoring the quality of a fuel stored in a fuel tank has been developed. Said device is preferably provided for a diesel-powered vehicle. Thus, the fuel is preferably diesel fuel. The device is characterized in that means are provided for determining the boiling point of the fuel.

Furthermore, within the scope of the invention a method for monitoring the quality of a fuel stored in a fuel tank has also been developed. Said method is preferably provided for a diesel-powered vehicle. Thus, the fuel is preferably diesel fuel. The method is characterized in that the boiling point of the fuel or a deviation of said boiling point from a normal value is measured.

During the analysis of real injection pumps that have failed, it has been recognized that an excessively low boiling point of the fuel can result in the fuel degassing. Consequently, bubbles form in the injection pump, in which the necessary lubrication is no longer provided locally. Furthermore, the lubrication effect relies on the fuel comprising a certain minimum viscosity. A low boiling point is also correlated with a low viscosity. Thus, overall the boiling point (initial boiling point, IBP) is a particularly good direct indicator of those abnormalities of the fuel that cause particularly expensive damage.

In a particularly advantageous embodiment of the invention, the means for determining the boiling point of the fuel comprise a transmitter and a receiver for ultrasound. In this case, the transmitter and/or the receiver can advantageously be coupled to the fuel, in particular by sound in solids, in order to guarantee very low-loss transmission. It has been recognized that the boiling point of the fuel can be determined by passing ultrasonic waves through the fuel and measuring the intensity of the ultrasound emitted from the fuel frequency-dependently and depending on the stimulation amplitude as a measure of the boiling point. Ultrasonic waves of sufficient amplitude produce such strong pressure minima in the fuel locally that the fuel evaporates, and bubbles of evaporated fuel pass through the liquid phase of the fuel. Said vapor cavitation bubbles of fuel are not stable, but collapse because of the external pressure of the liquid phase that is enveloping them. From the location of such a collapse, a microscopic vapor shock propagates through the fuel as a sound wave. The stimulation amplitude, and thereby the sound pressure in the fuel, from which vapor cavitation bubbles arise from the fuel and disappear again, now depend on the boiling point of the fuel. Thus, the number and/or intensity of microscopic vapor shocks arising during the dissolution of vapor cavitation bubbles is/are advantageously measured.

The occurrence of vapor cavitation is directly due to the local boiling of the fuel, since as a result the vapor arises from which the vapor cavitation bubbles form. However, the occurrence of vapor cavitation is also promoted by low viscosity of the fuel, since the coupling of ultrasound is then less attenuated. The number and/or intensity of microscopic vapor shocks is thereby also a measure of the viscosity of the fuel. A larger number and/or a higher intensity can thus not only be considered to be a sign of a reduced boiling point, but also as a sign of reduced viscosity. Thus, two parameters that are critical with respect to injection systems can be monitored jointly with one measurement.

The collapse of a vapor cavitation bubble is a sudden pressure equalization between the liquid phase of the fuel and the vapor cavitation bubble that is enclosed therein, which has just arisen from a pressure minimum. Said pressure equalization produces an undamped bang, which is maximally aperiodic and the frequency spectrum of which for a Fourier decomposition therefore contains very many high-frequency components. In order to separate the signal caused by the vapor shocks from other signal components, frequency components of the ultrasound emitted by the fuel above a cutoff frequency are therefore advantageously considered to be caused by microscopic vapor shocks.

A high sound pressure is necessary for producing vapor cavitation, but at the same time a "random sample" of a small volume within the tank is sufficient for most applications. In order to achieve at least a sufficient sound pressure in said small volume, in the device according to the invention the transmitter is advantageously disposed relative to the fuel tank so that said transmitter focusses the intensity of the ultrasound on at least one location in the interior thereof The pressure minima produced in fuel by the ultrasound may not only evaporate the fuel locally, but can also stimulate gases dissolved in the fuel to bubble out. In addition, contamination of the fuel with said gases, such as for example air, can result in localized dry running in the injection system. In addition, said gas bubbles that arise from bubbling out are not stable, but dissolve spontaneously again. Advantageously, the number and/or the intensity of the dissolution events of gas bubbles that are formed from gases dissolved in the fuel is/are therefore measured. Such a dissolution arises from states in which the gas dissolves in the fuel again. This is a diffusive process that runs slowly compared to vapor cavitation. The sound produced in such a dissolution event therefore contains fewer high-frequency components in the Fourier decomposition thereof. In order to extract said signal component, frequency components of the ultrasound emitted by the fuel below a cutoff frequency are therefore advantageously assessed as being caused by gas bubble dissolving events.

In a further particularly advantageous embodiment of the invention, a reduced boiling point of the fuel is assessed as a signal of contamination with gasoline, water or air. These are the foreign substances that occur in diesel fuel most often and at the same time cause the greatest damage.

A vapor cavitation bubble always forms if the local pressure falls below the vapor pressure of the fuel. It collapses if the external pressure falls below the vapor pressure of the fuel in the bubble. Using the number and/or intensity of microscopic vapor shocks, not only the boiling point of the fuel can thus be determined, but also the vapor pressure thereof under the current conditions in the tank.

The transmitter and the receiver for the ultrasound can be separate units. The transmitter and receiver can also be identical, however. For example, the piezoelectric effect is reciprocal, so that a piezoelectric transducer is suitable both as a transmitter and also as a receiver. The ultrasound is coupled into the fuel and the ultrasound emitted by the fuel is measured alternately. The combination of the transmitter and receiver in one unit has inter alia the advantage that only one point on the fuel tank is required, for example at the lowest point of the fuel tank, so that the device is still effective even at a low fill level.

Alternatively, a separate receiver for the ultrasound from the transmitter gives the possibility of carrying out frequency filtering before the receiver and filtering out the stimulation frequency. As a result, the signal generated by the fuel can still be detected with good resolution while the stimulation is occurring.

As a measure of the boiling point or of the vapor pressure, for example the stimulation amplitude can be assessed at which vapor cavitation is first indicated. This can for example be the stimulation amplitude at which the signal that is filtered with a high pass filter after the receiver exceeds a predetermined threshold value. However, the more detailed is the analysis of the frequency spectrum of the ultrasound emitted by the fuel, the smaller are the measurement errors.

Advantageously, the device is coupled to the controller of at least one valve that enables the discharge of fuel from the fuel tank. Thus, for example, when switching on the ignition, a check is first made as to whether the diesel in the fuel tank is clean. Only if this check is positive will the discharge of fuel from the tank be enabled. If the check is negative, the valve remains closed and the driver receives an alarm. In the event of any contamination of the fuel, only the tank and the line leading to the closed valve will then have to be cleaned or replaced.

The invention thus also concerns a fuel supply system. This comprises a fuel tank for storing fuel, an injection pump and a fuel line leading from the fuel tank to the injection pump that can be shut off by a valve. According to the invention, the valve is connected by means of a control line to a device according to the invention or with other means for carrying out the method according to the invention. Thus, the valve is shut off if the quality of the fuel does not meet a predetermined condition.

The condition can for example be a minimum value for the boiling temperature and/or for the viscosity. However, it can also be that certain foreign substances, such as for example water, gasoline or air, are not present or are only present in defined maximum concentrations in the fuel.

BRIEF DESCRIPTION OF THE DRAWINGS

Further measures that improve the invention are described in detail below together with the description of the preferred exemplary embodiments of the invention using a figure.

Exemplary embodiments

In the figure:

FIG. 1 shows an exemplary embodiment of a device according to the invention.

DETAILED DESCRIPTION

FIG. 1 shows an exemplary embodiment of the device according to the invention for protecting the injection pump 11 against unsuitable fuel. The fuel tank 1 is filled to about two thirds with fuel 3. In this case, it is diesel fuel. A piezoelectric thickness oscillator 2 that operates as a receiver 2a at the same time is disposed at the lowest point of the tank. A sinusoidal alternating voltage with a constant stimulation frequency and amplitude U increasing with time is applied to the thickness oscillator 2 by drive electronics 5. The sinusoidal time profile of the alternating voltage can also be replaced by a different time profile, for example a square wave profile. At alternating times with the stimulation, the ultrasound emitted by the fuel 3 is detected with the thickness oscillator 2 operating as a receiver 2a. Said signal is delivered to a measurement instrument 7 via a high pass filter 6 consisting of a capacitor C and a resistor R. Instead of said analog high pass filter, digital signal processing can be used.

From a defined stimulation amplitude U, vapor cavitation bubbles 4 that are filled with fuel vapor form in the fuel 3. From the points 4a at which vapor cavitation bubbles 4 collapse, ultrasound propagates towards the receiver 2a. Said ultrasound contains particularly many high-frequency components that can pass through the high pass filter 6. The stimulation amplitude U at which the signal at the measurement instrument 7 exceeds a predetermined threshold value is assessed as a measure of the boiling point or vapor pressure of the diesel fuel 3. Only if said boiling point or vapor pressure lies within a normal range will the solenoid valve 9 in the fuel line 10 be opened via a control line 8 emanating from the measurement instrument 7. This enables fuel to pass from the tank 1 into the injection pump 11. If contamination of the fuel 3 is detected, the solenoid valve 9 remains in the position thereof shown in FIG. 1 and the injection pump 11 is protected against damage.

The invention claimed is:
1. A device for monitoring the quality of a fuel (3) stored in a fuel tank (1), the device comprising:
   an ultrasonic transmitter (2);
   an ultrasonic receiver (2a);
   a measuring device (5);
   wherein the ultrasonic transmitter (2) emits a signal into the fuel (3), the signal causing bubbles to form in the fuel (3) and collapse, the collapse of the bubbles altering the signal;

wherein the ultrasonic receiver (2a) receives the altered signal; and wherein the measuring device (5) determines a boiling point of the fuel (3) based on the altered signal and the quality of the fuel (3) is determined based on the determined boiling point of the fuel (3);

wherein the fuel (3) is prevented from entering an injection pump (11) when the determined quality of the fuel (3) indicates contamination of the fuel (3).

2. The device as claimed in claim 1, wherein the device is for a diesel powered vehicle.

3. The device as claimed in claim 1, characterized in that the means comprise a transmitter (2) and a receiver (2a) for ultrasound.

4. The device as claimed in claim 3, characterized in that the transmitter (2) is coupled to the fuel (3).

5. The device as claimed in claim 3, characterized in that the receiver (2a) is coupled to the fuel (3).

6. The device as claimed in claim 3, characterized in that the transmitter (2) and the receiver (2a) are coupled to the fuel (3).

7. The device as claimed in claim 6, characterized by such an arrangement of the transmitter (2) relative to the fuel tank (1) that the transmitter focusses the intensity of the ultrasound on at least one point in the interior of the tank.

8. A method for monitoring the quality of a fuel (3) stored in a fuel tank (1), by a device having an ultrasonic transmitter (2), an ultrasonic receiver (2a), and a measuring device (5), the method comprising:

emitting a signal into the fuel (3), by the ultrasonic transmitter (2), the signal causing bubbles to form in the fuel (3) and collapse, the collapse of the bubbles altering the signal;

receiving, by by the ultrasonic receiver (2a), the altered signal; and determining a boiling point of the fuel (3), by the measuring device (5), based on the altered signal;

determining the quality of the fuel (3) based on the determined boiling point of the fuel (3);

preventing the fuel (3) from entering an injection pump (11) when the determined quality of the fuel (3) indicates contamination of the fuel (3).

9. The method according to claim 8, characterized in that a reduced boiling point of the fuel (3) is assessed as a signal of contamination with gasoline, water or air.

10. The method as claimed in claim 8, wherein the method monitors the quality of a fuel stored in a fuel tank of a diesel powered vehicle.

11. The method as claimed in claim 8, characterized in that ultrasonic waves are passed through the fuel (3) and the intensity of the ultrasound emitted by the fuel (3) is measured depending on the stimulation amplitude (U) and frequency-dependently as a measure of the boiling point.

12. The method as claimed in claim 11, characterized in that the number of microscopic vapor shocks that arise during the dissolution of vapor cavitation bubbles (4) are measured.

13. The method as claimed in claim 11, characterized in that the intensity of microscopic vapor shocks that arise during the dissolution of vapor cavitation bubbles (4) is measured.

14. The method according to claim 11, characterized in that the number of the dissolution events of gas bubbles that have been formed by gases dissolved in the fuel (3) are measured.

15. The method according to claim 11, characterized in that the intensity of the dissolution events of gas bubbles that have been formed by gases dissolved in the fuel (3) is measured.

16. The method as claimed in claim 11, characterized in that the number and intensity of microscopic vapor shocks that arise during the dissolution of vapor cavitation bubbles (4) is/are measured.

17. The method as claimed in claim 16, characterized in that frequency components of the ultrasound emitted by the fuel (3) above a cutoff frequency are assessed as being caused by microscopic vapor shocks.

18. The method according to claim 11, characterized in that the number and intensity of the dissolution events of gas bubbles that have been formed by gases dissolved in the fuel (3) is/are measured.

19. The method as claimed in claim 18, characterized in that frequency components of the ultrasound emitted by the fuel (3) below a cutoff frequency are assessed as being caused by dissolution events of gas bubbles.

20. A fuel supply system comprising a fuel tank (1) for storing fuel (3), an injection pump (11) and a fuel line (10) leading from the fuel tank (1) to the injection pump and that can be shut off by a valve (9), characterized in that the valve (9) is connected by a control line (8) to a device for carrying out a method according to claim 11, so that the valve (9) is shut off if the quality of the fuel (3) does not meet a predetermined condition.

* * * * *